United States Patent [19]

Wall et al.

[11] Patent Number: 5,049,668
[45] Date of Patent: Sep. 17, 1991

[54] 10,11-METHYLENEDIOXY-20(RS)-CAMPTOTHECIN ANALOGS

[75] Inventors: Monroe E. Wall, Chapel Hill; Mansukh C. Wani, Durham; Allan W. Nicholas; Govindarajan Manikumar, both of Raleigh, all of N.C.

[73] Assignee: Research Triangle Institute, Research Triangle Park, N.C.

[21] Appl. No.: 407,749

[22] Filed: Sep. 15, 1989

[51] Int. Cl.$^5$ ............... A61K 31/47; C07D 491/147; C07D 491/22
[52] U.S. Cl. ............... 540/481; 540/597; 544/61; 544/361; 546/48
[58] Field of Search ............... 546/48; 544/61, 361; 540/481, 597

[56] References Cited

U.S. PATENT DOCUMENTS

| | | | |
|---|---|---|---|
| 4,031,098 | 6/1977 | Sugasawa | 424/258 |
| 4,473,692 | 9/1984 | Miyasaka et al. | 546/48 |
| 4,545,880 | 10/1985 | Miyasaka et al. | 204/158 |
| 4,604,463 | 8/1986 | Miyasaka et al. | 544/125 |
| 4,894,456 | 1/1990 | Wall et al. | 546/41 |
| 4,914,205 | 4/1990 | Sawada et al. | 546/70 |

FOREIGN PATENT DOCUMENTS

| | | |
|---|---|---|
| 0074256 | 3/1983 | European Pat. Off. |
| 0220601 | 3/1984 | European Pat. Off. |
| 0321122 | 6/1989 | European Pat. Off. ......... 546/48 |
| 5905188 | 6/1982 | Japan |
| 57-116015 | 7/1982 | Japan |
| 5951289 | 9/1982 | Japan |
| 6185319 | 3/1984 | Japan |
| 6150985 | 5/1984 | Japan |
| 59-51287 | 7/1984 | Japan |
| 6185389 | 10/1984 | Japan |

OTHER PUBLICATIONS

*Cancer Research* (1989), vol. 49; 4385–5489, "DNA Topoisomerase I-Meditated DNA Cleavage and Cytotixicity of Camptothecin Analogues", Hisang et al.
*Cancer Research* (1989); vol. 49, 1465–1469, "Structure-Activity Study of the Actions of Camptothecin Derivatives on Mammalian Topoisomerase I . . ." Jaxel et al.
*The Journal of Biological Chemistry* (1985, 260, 14873–14878, "Camptothecin Induces Protein-Linked DNA Breaks via Mammalian DNA Topoisomerase I" Hsiang et al.

(List continued on next page.)

*Primary Examiner*—Mukund J. Shah
*Assistant Examiner*—Matthew V. Grumbling
*Attorney, Agent, or Firm*—Oblon, Spivak, McClelland, Maier & Neustadt

[57] ABSTRACT

A camptothecin analog having the structure shown below:

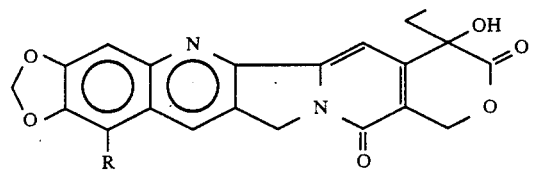

wherein R is $NO_2$, $NH_2$, $NHCOCHR^1NR^2R^3$, where $R^1$ is the side-chain of an α-amino acid and $R^2$ and $R^3$, independently are hydrogen or a lower alkyl group or $R^3$ is a peptide unit containing 1-3 amino acid units bonded to the nitrogen through a peptide bond, $NHCO-C_{2-8}$-alkylene-X or $NHCO-C_{2-8}$-alkenylene-X, where X is COOH or $CONR^2-(CH_2)_n-NR^2R^3$, $n=1-10$ and $R^2$ and $R^3$ are as defined above, $NHCO-Z-(CH_2)_n-NR^2R^3$, where z=oxygen or NH, or

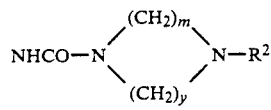

where m+y=3-6 and salts thereof.

18 Claims, 1 Drawing Sheet

CAMPTOTHECIN (CPT)     CPT-SODIUM SALT 10,11-20(RS)-MDCPT    9-AMINO-10,11-20(RS)-MDCPT    9-GLYCINAMIDO-10,11-20(RS)-MDCPT, HYDROCHLORIDE 10,11-20(RS)-MDCPT-SODIUM SALT

OTHER PUBLICATIONS

*J. Med. Chem.* (1980), 23, 544–560; "Plant Antitumor Agents. 18.[1] Synthesis and Bilogical Activity of Camptothecin Analogues", Wani et al.

*J. Med. Chem.* (1989); 29, 1553-1555, "Plant Antitumor Agents 22.[1] Isolation of 11-Hydroxycamptothecin From Camptotheca Acuminata Decne . . . " Wall et al.

*Journal of Labelled Compounds and Radiopharmaceuticals* (1981); 18; 319–329, "The Preparation of Tritium and Deuterium-Labelled Camptothecin", Ronman et al.

*J. Medicinal Chemistry* (1987), 30; 1774-1779, "Plant Antitumor Agents 25.[1] Total Synthesis and Antileukemic Activity of Ring A . . . "; Wani et al.

*J. Medicinal Chemistry* (1990), 33, 972-978, "Plant Antitumor Agents. 29[1] Synthesis and Biological Activity of Ring D and Ring 3 . . . " Nicholas et al.

J. Org. Chem. (1974), 39, 303-311; "Synthesis of Some DE and CDE Ring Analogs of Camptothecin", Plattner et al.

J. of Am. Chem. Soc. (1972); 94, 8615, "Synthesis of Some DE and CDE Ring Analogs of Camptothecin" Plattner et al.

*J. Org. Chem.* (1974); 39, 3430-3432, "Synthesis of Biological Evaluation of De-AB-Camptothecin", Danishefsky et al.

Govindachari et al., 453-454, "9-Methoxycamptothecin. A New Alkaloid from Mappia Foetida Miers".

Huaxue Xuebao, (1984); 42, 42-50, "Mass Spectrometric Study of Camptothecin and Related Compounds", Yang et al. CA 100:139434W.

Hua Hsueh Hsueh Pao (1975), 33, 71-74, "Studies on the Derivatives of Camptohecin"; Pan et al. CA 115 629p.

Hua Hsueh, (1977), 2, 51–54; "Studies on the Constituents of Camptotheca Acuminate Done". I . . . Tien et al. Abstract only.

*J. Nat. Prod.* (1979), 42, 475-477, "Plant Anticancer Agents. X. Ioslation of Camptothecin and 9-Methoxycamptothecin From Ervatamia . . . " Gunasekera et al., Abstract.

Chung-Kuo Yao Li Hsueh Pai, (1980), 1, 109-112; "Distribution and Excretion of Camptothecin Suspension and Sodium Camptothecin In Mice"; Chen et al. Abstract.

*Heterocycles* (1980), 14, 951-953; "A Facile Synthesis of (±)-Camptothecin by Enamine Annelation," Kametani et al. Abstract only.

Hua Hsueh Hsueh Pai, (1981), 39, 171-178; "Total Synthesis of Di-10-Hydroxy-Camptothecin and Di-1-0-Methoxycamptothecin"; Cai et al. Abstract only.

*Heterocycles* (1981), 16, 1713-1717; "A Selective One-Step Introduction of Hydroxylic Functions at the C-5 and C-7 Positions of . . . "; Miyasaka et al. Abstract.

Yaoxue Xuebao, (1984), 19, 63-68; "Studies on Polyphase Liposome of Camptothecin", PL-CSA: Luo et al. Abstract only.

Aichi Ika Daigaku Igakkai Zasshi; (1983), 11, 286-293, "Effects on an Antitumor Alkaloid, Camptothecin and its Derivatives on Cell Growth . . . " Nagata et al. Abstract.

*Biochem. Pharmacol* (1985), 34, 1225-1230, "Action of Camptothecin and its Derivatives on Deoxyribonucleic Acid", Fukada. Abstract only.

*Proc. Annu. Meet. Am. Assoc. Cancer Res.* (1988); 29, A1080, "Structue-Activity Study of the Relation Between Topoisomerase I Inhibition and Antitumor" . . . Abstract.

*Proc. Annu. Meet. Am Assoc. Cancer Res.* (1989); 8, A1019, "A Clinical Study of A Camptothecin Derivative, CPT-11 on Hematological Malignancies"; (Mtg. Abstract).

*Proc. Ann. Meet. Am Assoc. Cancer Res.* (1989), 30; A2485, "Irreversible Trapping of the DNA-Topoisomerase I Covalent Complex and Affinity Labeling of . . . " Abstract.

Yao Hsueh Hsueh Pao, (1988), 23, 186-188, "A New Alkaloid-19-Hydroxy-Camptothecin" Lin et al. Abstract only.

*J. Med. Chem.* (1989), 32, 715-720, "Modification of the Hydroxy Lactone Ring of Camptothecin: Inhibition of Mammalian Topoisomerase I and . . . ", Mong et al. Abstract.

*Science* (1989), 246, 1046-1048, "DNA Topoisomerase I-Targeted Chemotherapy of Human Colon Cancer in Xenografts"; Giovanella et al. Abstract only.

*Proc. Annu. Meet. Am. Assoc. Cancer Res.* (1989), A2476; "Structure-Activity Studies of 20(S)-Captothecin Analogs (Meeting Abstract)". Abstract only.

Wani et al., J. Med. Chem.; vol. 23, No. 5, pp. 554-560 (198)).

Wani et al., J. Med. Chem., vol. 29; No. 11, pp. 2358-2363 (1986).

Wani et al., J. Med. Chem.; vol. 30, 1774 (1987).

10,11-METHYLENEDIOXY-20(RS)-CAMPTOTHECIN ANALOGS

BACKGROUND OF THE INVENTION

1. Field of the Invention

The present invention relates to camptothecin analogs which are useful as antitumor agents. More specifically, the invention is directed to water-insoluble and water-soluble derivatives of 10,11-methylenedioxy-20(RS)-camptothecin.

2. Discussion of the Background

Camptothecin is a pentacyclic alkalloid initially isolated from the wood and bark of *Camptotheca acuminata* by Wall et.al. (M. E. Wall, M. C. Wani, C. E. Cook, K. H. Palmer, A. T. McPhail, and G. A. Sim, *J. Am. Chem. Soc.*, 94:388 (1966)).

Camptothecin is highly biologically active and displays strong inhibitory activity toward the biosynthesis of nucleic acids. Additionally, camptothecin exhibits potent anti-tumor activity against experimentally transplanted carcinoma such as leukemia L-1210 in mice or Walker 256 tumor in rats.

Several methods for the synthesis of camptothecin and camptothecin analogs are known. These synthetic methods include (i) methods in which naturally occurring camptothecin is synthetically modified to produce a number of analogs and (ii) totally synthetic methods. U.S. Pat. Nos. 4,604,463; 4,545,880; and 4,473,692 as well as European Patent Application 0074256 are examples of the former type of synthetic strategy. Additional examples of this strategy can be found in Japanese Patents 84/46,284; 84/51,287; and 82/116,015. These methods require naturally occurring camptothecin which is difficult to isolate and hence these methods are not suitable for the production of large quantities of camptothecin or analogs.

Examples of a variety of totally synthetic routes to camptothecin and camptothecin analogs can be found in the following references: *Sci. Sin. (Engl. Ed)*, 21(1), 87–98 (1978); *Fitoterpapia*, 45(3), 87–101 (1974); *Yakugaku Zashi*, 92(6), 743–6 (1972); *J. Org. Chem.*, 40(14), 2140–1 (1975); *Hua Hsueh Hsueh Pao*, 39(2), 171–8 (1981); *J. Chem. Soc., Perkin Trans 1*, (5) 1563–8 (1981); *Heterocycles*, 14(7), 951–3 (1980); *J. Amer. Chem. Soc.*, 94(10), 3631–2 (1972); *J. Chem. Soc. D*, (7), 404 (1970) and U.S. Pat. No. 4,031,098.

Synthetic studies directed to camptothecin analogs have also been conducted by the present inventors and are disclosed in *J. Med. Chem.*, 23(5), 554–560 (1980); *J. Med. Chem.*, 29(8), 1553–1555 (1986) and *J. Med. Chem.*, 29(11), 2358–2363(1986) for example.

Water-solubility is an important criterion in developing potential antitumor compounds for pharmaceutical use. Most camptothecin analogs known in the art have relatively poor water-solubility. A need exists for additional water-soluble camptothecin analogs and methods for preparing the same.

SUMMARY OF THE INVENTION

Accordingly, one object of the present invention is to provide water-soluble camptothecin analogs containing the 10,11-methylenedioxy moiety.

A further object is to provide camptothecin analogs which are not only water-soluble but which exhibit high cyctotoxic activity and which can be readily prepared.

These and other objects which will become apparent from the following specification have been achieved by the process of the present invention and the compounds produced thereby.

More specifically, the invention is directed to water-soluble and water-insoluble compounds which are derivatives of 10,11-methylenedioxy-20(RS)-camptothecin (10,11-MDCPT) which itself is a highly active camptothecin analog. 9-Nitro-10,11-MDCPT, 9-amino-10,11-MDCPT and various water-soluble analogs are prepared from 10,11-MDCPT.

BRIEF DESCRIPTION OF THE DRAWING

A more complete appreciation of the invention and many of the attendant advantages thereof will be obtained as the same becomes better understood by reference of the following detailed description when considered in connection with the accompanying drawing, wherein.

DETAILED DESCRIPTION OF THE PREFERRED EMBODIMENTS 10,11-MDCPT is an extremely potent camptothecin analog and is one of the most potent inhibitors of the enzyme topoisomerase I known. 10,11-MDCPT is also highly active in such in vitro cytotoxicity tests as the 9KB and 9PS tests and shows inhibitions of $ED_{50}$ of the same or higher order than camptothecin itself. 10,11-MDCPT is also very potent in the L-1210 leukemia in vivo life prolongation assay. The synthesis of 10,11-MDCPT is known and described in Wani et.al., *J. Med. Chem.*, 29 (11), 2358–2363 (1986) and in U.S. application Ser. No. 07/032,449, filed Mar. 31, 1987.

Figure 1:
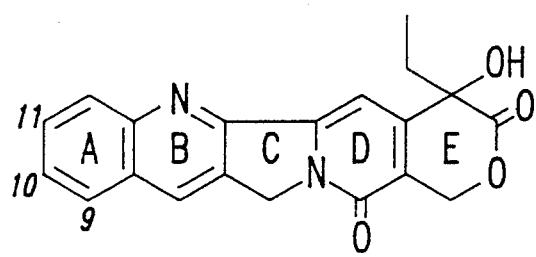
FIG. 1 shows the structure CPT and derivatives thereof.
Figure 1:
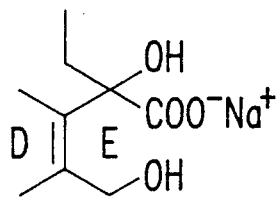
Figure 1:
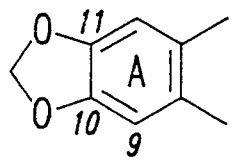
Figure 1:
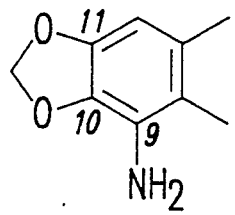
Figure 1:
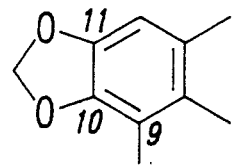
Figure 1:
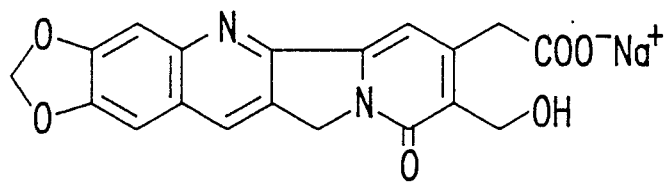

Novel analogs of camptothecin have been prepared, all of which contain the 10,11-methylenedioxy moiety. The structures of these compounds and their relation to camptothecin are shown in FIG. 1.

The 10,11-methylenedioxy (MD) group confers striking and unexpected improvements on the in vitro and in vivo activity found in the camptothecin molecule with particular reference to anti-tumor activity. Thus, Javier et.al., *Cancer Res.*, 49, 1465 (1989), and Hsiang et.al., *Cancer Res.*, 49, in press (1989), have shown that 10,11-20(RS)-MDCPT has two to three times the potency of camptothecin in the inhibition of topoisomerase I. Inhibition of this enzyme has been shown by Javier et.al. (loc cit) to be very well correlated with increase in in vivo anti-tumor and anti-leukemic activity. Moreover, although the sodium salts of CPT and the sodium salts of almost all other CPT analogs are very weak in the inhibition of topoisomerase I, the sodium salt of 10,11-20(RS)-MDCPT is as active as CPT. In in vivo studies with L-1210 mouse leukemia, the 10,11-20(RS)-MDCPT and 10,11-20(RS)-MDCPT sodium salt are considerably more potent than CPT or CPT sodium salt, respectively. See Wani et. al., *J. Med. Chem.*, 30., 1774 (1987). Other preferred compounds of this invention are 9-amino-10,11-20(RS)-MDCPT and 9-glycinamido-10,11-20(RS)-MDCPT hydrochloride. These also show high inhibition of topoisomerase I. Hence, 10,11-20(RS)-MDCPT and all of its analogs have unexpectedly high potency conveyed by the 10,11-methylenedioxy moiety. In contrast, a compound with quite similar structure, 10,11-dimethoxy-20(RS)-CPT, is totally inactive, Wani et.al., *J. Med. Chem.*, 23, 554 (1980). The 10,11-MD moiety is held rigidly in the plane of ring A of CPT (See structure in FIG. 1), and this contributes to the additional biological activity unexpectedly noted with all of these compounds.

It has been discovered that water-soluble analogs of 10,11-MDCPT can be prepared by opening the lactone ring of 10,11-MDCPT to form water-soluble salts and by derivatizing 10,11-MDCPT to form 9-nitro-10,11-MDCPT and 9-amino-10,11-MDCPT, the latter of which can be further derivatized to provide water soluble salts. These new derivatives exhibit substantially improved water-solubility and retain a high level of cytotoxicity. The water insoluble compounds (9-nitro-10,11-MDCPT and 9-amino-10,11-MDCPT) exhibit such high potency and activity that alternate formulations are warranted.

The interaction of pharmaceutical compounds with biological systems is highly specific and intimately related to the three-dimensional structure of a compound and the chemical functionality present on the pharmaceutical compound. It is well known in the pharmaceutical art that structural changes as simple as the use of an opposite enantiomer can result in complete loss of biological activity and in some instances even opposite biological activity. Surprisingly, it has been discovered that it is possible to hydrolyze the lactone ring of 10,11-MDCPT and yet retain substantial biological activity while also enhancing water-solubility.

In one embodiment, the water-soluble analogs of the present invention are prepared by hydrolyzing the lactone ring of 10,11-MDCPT by utilizing one equivalent of an aqueous alkali metal hydroxide. The hydrolysis is preferably carried out in an aqueous solution. The resulting product is the alkali metal salt of 10,11-MDCPT in which the lactone ring has been opened to form the corresponding hydroxyl and carboxylate functional groups, as shown below, where M+ is a monovalent metal cation and R is hydrogen.

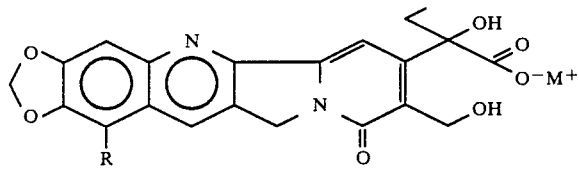

Preferred alkali metal hydroxides are potassium hydroxide and sodium hydroxide, with sodium hydroxide being particularly preferred.

Obviously, alkali metal hydroxide concentrations above or below one equivalent may be used in the present process, although concentrations below one equivalent result in incomplete formation of the metal salt and unnecessary separation operations. Likewise, alkali metal hydroxide concentrations in excess of one equivalent may be used although the excess alkali metal hydroxide must be subsequently removed from the product.

The hydrolysis reaction may be conducted at any temperature which allows adequate reaction of the 10,11-MDCPT and alkali metal hydroxide so long as the temperature is sufficiently low to prevent decomposition of the starting materials. Suitable temperatures are from about 5°–50° C. with preferred temperatures being approximately room temperature.

In the hydrolysis reaction, the 10,11-MDCPT is generally, but not necessarily suspended in a suitable solvent such as methanol or aqueous methanol and treated with aqueous alkali metal hydroxide. To increase the rate of reaction, the reaction mixture may be gently heated. After cooling, the 10,11-MDCPT metal salt may be isolated by standard recrystallization or chromatographic processes following removal of the methanol and water solvents. Any water miscible solvent conventionally used with camptothecin analogs may be used instead of methanol.

Alkali metal salts of other 10,11-MDCPT analogs may also be prepared by analogous reactions. For example, 9-nitro-10,11-MDCPT, 9-amino-10,11-MDCPT, and the 9-amido-10,11-MDCPT derivatives described below may also be hydrolyzed by a process analogous to the process described above for 10,11-MDCPT to provide the corresponding monovalent metal salts of these derivatives.

The present invention also includes water-insoluble analogs which are prepared by first nitrating 10,11-MDCPT followed by reduction to form 9-amino-10,11-MDCPT. Using standard nitration reaction conditions ($H_2SO_4/HNO_3$) for the nitration of camptothecin itself, one obtains a mixture of the 12 and 9-nitro-camptothecin analogs with the 12-nitro analog present in considerable excess. A structure analysis of 10,11-MDCPT reveals that the 9- and 12-positions are available for nitration and the 10,11-methylenedioxy group appears to exhibit an analogous electronic influence on both the 9- and 12-positions. An analysis of the electronic and steric environments on the potential nitration positions of 10,11-MDCPT leads to the expectation that 10,11-MDCPT will nitrate in a manner similar to camptothecin itself and provide an excess of the 12-nitro analog. Quite unexpectedly, it was found that nitration of 10,11-MDCPT gives substantially the 9-nitro-10,11-MDCPT with only trace amounts of the 12-nitro analog. The present method, therefore, provides a surprisingly effective procedure for preparing the 9-nitro-10,11-MDCPT analog in high yield regioselectively.

The nitration reaction may be conducted using standard conditions for the nitration of aromatic compounds, and is generally conducted by dissolving/suspending 10,11-MDCPT in concentrated sulfuric acid with cooling and stirring followed by the addition of a slight excess of concentrated nitric acid. After stirring for a period of time sufficient to substantially complete the reaction, the solution is poured into water, ice or a ice/water mixture to provide the desired 9-nitro-10,11-MDCPT. Purification can be effected by standard extraction and recrystallization processes.

The 9-nitro-10,11-MDCPT may then be catalytically reduced using hydrogen and a hydrogenation catalyst such as platinum, palladium, etc or other conventional hydrogenation reactions. Preferably, the hydrogenation catalyst is present on an inert support such as powdered carbon. Reduction of the 9-nitro analog to the 9-amino analog is conducted using standard hydrogenation solvents and hydrogen pressure conditions. Generally, the nitro compound is dissolved/suspended in ethanol and contacted with a hydrogen atmosphere. The concentration of catalyst and of the nitro compound in the solvent is not critical. Generally, concentrations of the nitro compound from about 1 mg/ml to 3 mg/ml are used with catalyst concentrations ranging from about 20–100 wt. %. The preferred solvent is absolute ethanol although other conventional inert solvents may be used.

The hydrogenation reaction is generally conducted at ambient temperature although temperatures above or below ambient temperature may be used so long as the camptothecin analog is not decomposed. Hydrogenation reaction times vary with the amount of nitro compound to be hydrogenated and can be easily determined by one skilled in the art. Generally, reaction times ranging from 2–30 hours are sufficient to hydrogenate 9-nitro-10,11-MDCPT.

Water-soluble derivatives of 10,11-MDCPT can be prepared by reacting the amino group of 9-amino-10,11-MDCPT with appropriately protected amino acids and peptides, $C_{4-10}$ anhydrides or the corresponding ester-acid acid halide derivatives. For example, 9-amino-10,11-MDCPT may be reacted with the carboxylic acid group of an α-amino acid to give compounds having the structure shown below:

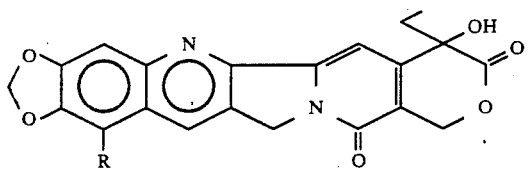   (I)

in which R is the group —NHCOCHR$^1$NR$^2$R$^3$, where R$^1$ is the side-chain of an α-amino acid, preferably the side chain of a D or L-isomer of one of the naturally occurring amino acids, preferably one of the 20 commonly occurring amino acids, and R$^2$ and R$^3$ are, independently, hydrogen or a lower alkyl group having 1–6 carbon atoms. Additionally, R$^3$ may be a peptide unit containing 1–3 amino acid units bonded to the nitrogen atom through a peptide bond. These water-soluble analogs, therefore, contain from 1–4 peptide units bonded to the 9-amino nitrogen atom by means of a peptide bond. Obviously, amino acids which are not naturally occurring may also be used to prepare water-soluble 9-amido-10,11-MDCPT derivatives so long as the amino acid has a carboxylic acid, acid halide or other reactive acyl functionality to form the required peptide bond with the 9-amino group of 9-amino-10,11-MDCPT. Preferred side chains R$^1$ are alkyl and aralkyl groups containing 2–20, preferably 2–10 carbon atoms.

Generally, these amino acid and peptide-containing derivatives are prepared using amino acids and peptides in which reactive functional groups such as amino groups and carboxylic acid groups are protected using standard amino acid protecting groups. For example, when preparing a derivative from an amino acid such as glycine, one can protect the amino group of glycine with tBOC chloride to prepare the reactive tBOC-protected amino acid. Appropriately protected amino acids are also available commercially. The protected amino acid is reacted with 9-amino-10,11-MDCPT and the tBOC group is then removed to give the water-soluble salt of the 9-glycinamido derivative, for example.

If desired, free amino groups on the amino acids or peptides may be derivatized by known nitrogen alkylation reactions, i.e., reaction with alkyl halides, to provide mono or dialkylamino acid amido derivatives as shown above (R$^2$ and/or R$^3$=alkyl). Preferably, free amino groups are derivatized to form $C_{1-3}$ mono or dialkylamino groups.

Dibasic amino acids such as arginine, histidine, lysine, etc. and dicarboxylic amino acids such as aspartic acid, glutamic acid, etc. may be used for one or more of the amino acids in the amino acid or peptide derivatives described above. If desired, standard addition salts may be prepared by reacting the free amino groups of any amino acid with a mineral acid such as HCl, HBr, $H_3PO_4$ or organic acids such as malic, maleic or tartaric acids. Likewise, free carboxylic acid groups on any amino acid may be derivatized by the formation of monovalent metal cation salts, ammonium salts or quaternary ammonium salts by the addition of monovalent metal hydroxides, ammonia or amines. Quaternary ammonium salts may be formed with primary, secondary or tertiary amines in which the nitrogen atom of the amine contains 1, 2 or 3 lower alkyl or substituted lower alkyl groups. Substituted lower alkyl groups containing one or more hydroxyl groups are preferred. Sodium salts, triethylammonium and triethanol ammonium salts are particularly preferred.

Other water-soluble derivatives can also be prepared by reacting 9-amino-10,11-MDCPT with a $C_{4-10}$ saturated or unsaturated acid anhydride, the corresponding ester-acid halide or other reactive acyl derivatives to provide analogs having structure I in which R is NHCO-$C_{2-8}$-alkylene-X and NHCO-$C_{2-8}$-alkenylene-X where X=COOH. The reaction is optionally carried out in a suitable solvent and produces the corresponding half acid. For example, reaction of 9-amino-10,11-MDCPT with glutaric anhydride gives the 9-glutaramide half acid. Likewise, reaction of 9-amino-10,11-MDCPT with the $C_{1-6}$ ester-acid halide corresponding to glutaric anhydride results in the 9-glutaramide half acid ester. Conventional hydrolysis of the ester produces the half acid. Water solubility is then imparted in each case by reaction with one equivalent of any of the bases from above.

The reaction of 9-amino-10,11-MDCPT with the anhydride or other reactive acyl compound is preferably carried out in the presence of a weak base such as a secondary or tertiary amine to facilitate the formation of the product amide. Suitable amines include cyclic amines such as pyridine as well as lower alkyl secondary and tertiary amines.

The free acid group of the amino acid amide half acid may be further coupled with a suitable alkylene diamine (NHR$^2$-(CH$_2$)$_n$—NR$^2$R$^3$) to give amino amides in which the R group in structure I is —NH-A'-NR$^2$-(CH$_2$)$_n$-NR$^2$R$^3$, where n=1–10, preferably 2–6, and A' is a $C_{4-10}$ acyl-alkylene-acyl or $C_{2-8}$ acyl-alkenylene-acyl group i.e., R is NHCO-$C_{2-8}$-alkylene-X or NHCO-C—$C_{2-8}$-alkenylene-X where X is COOH or CONR$^2$—(CH$_2$)$_n$—NR$^2$R$^3$. For example, the reaction of 9-glutaramido-10,11-MDCPT with a suitable diamine such as 3-(dimethylamino)-1-propylamine gives the corresponding amino acid amide as shown below.

10,11-MDCPT—NHCO(CH$_2$)$_3$COOH +

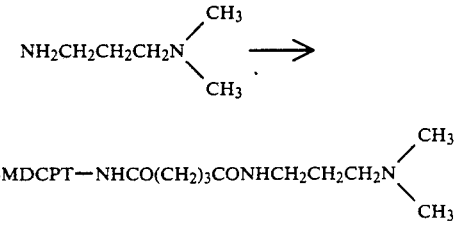

Acid and base addition salts of these derivatives may also be prepared in a manner analogous to that described above.

In another embodiment, water-soluble urea and urethane analogs can be prepared by reacting 9-amino-10,11-MDCPT with phosgene followed by reaction with an appropriate diamine or tertiary-amino alcohol to give compounds having the formula I in which R is -NHCO-Z(CH$_2$)$_n$—NR$^2$R$^3$, where Z is oxygen or NH and compounds in which R is

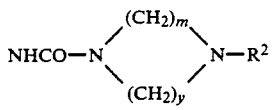

where m+y=3-6 and n, R$^2$ and R$^3$ are as defined above.

Suitable diamines are primary and secondary straight-chain, branched or cyclic diamines containing 3-15 carbon atoms. Examples of straight-chained and branched diamines include diaminoethane, 1,2- and 1,3-diaminopropane, 1,4-diaminoethane, etc. Examples of cyclic diamines included pyrazolidine, imidazolidine, piperazine, etc. Preferred diamines are diamines in which one of the amino groups is derivatized to form a di-loweralkylamino group such as, for example, NH$_2$CH$_2$CH$_2$CH$_2$N(CH$_2$CH$_3$. The reaction of 9-amino-10,11-MDCPT with phosgene followed by a diamine is represented below.

9-amino-10,11-MDCPT + CO(Cl$_2$) ⟶

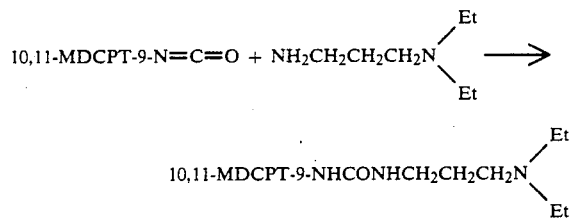

Tertiary-amino alcohols for the preparation of urethane analogs include N-di-C$_{1-6}$-alkylamino alkanols prepared from amino alkanols having 2-10 carbon atoms, for example, N-diethyl-aminoethanol.

Water soluble standard acid and base addition salts can be prepared from the urea and urethane analogs in a manner similar to that described above for other amino and carboxylic acid group-containing analogs.

Particularly preferred derivatives within the scope of the present invention are 10,11-MDCPT analogs having glycinamido, succinamido, glutaramido, (4-methylpiperazino)carbonylamino, N,N-dimethyl-aminopropylamido-glutaramido and (N,N-diethylaminoethoxy)carbonylamino substituents at the 9-position and the water soluble salts thereof.

The salts of the present invention exhibit substantially improved water-solubility relative to conventional camptothecin analogs and may be formulated into solid and aqueous pharmaceutical compositions by conventional methods. The analogs are active in standard cytotoxicity tests and are inhibitors of topoisomerase I.

Other features of the invention will become apparent from the following descriptions of preferred embodiments which are given for illustration of the invention and are not intended to be limiting thereof.

EXAMPLES

Example 1

SYNTHESIS OF 9-AMINO-10,11-MDCPT

The title compound was prepared from 10.11-methylenedioxy-20(RS)-camptothecin (Wani et.al., *J. Med. Chem.* 29. 2358 (1986)) by the following two-step process:

Conversion of 10,11-MDCPT to 9-Nitro-10,11-MDCPT 10,11-MDCPT (332 mg, 0.847 mmol) was dissolved/suspended in conc. H$_2$SO$_4$ (5 mL), stirred and cooled to 0° C., and treated over 5 min with conc. HNO$_3$ (25 drops). After 1 hr. the brown solution was poured onto ice/H$_2$O (50 mL) to provide a yellow-orange precipitate which was collected by filtration (292 mg). Extraction of the filtrate with CHCl$_3$ (2×50 mL) provided additional material (83 mg) for a total yield of 375 mg (100%). Recrystallization from MeOH/CHCl$_3$ provided a 75% recovery of the title compound as a yellow powder: mp darkening above 255° C. with no melting below 350° C.: IR $\nu_{max}$ (KBr) 3430 (br), 2920, 1741 (lactone), 1654 (pyridone), 1596 (aromatic), 1525 (NO$_2$), 1450, 1343, 1242, 1191, 1154, 1043, 928, 785 and 565 cm$^{-1}$; $^1$H NMR (DMSO-d$_6$) δ 0.87 (t, 3, J=7 Hz, H-18), 1.85 (m, 2, H-19), 5.21 (s, 2, H-5), 5.41 (s, 2, H-17), 6.52 (s, 2, —OCH$_2$O—), 7.24 (s, 1, H-14), 7.78 (s, 1, H-12), 8.96 (s, 1, H-7).

Conversion of 9-Nitro-10,11-MDCPT to 9-Amino-10,11-MDCPT

A suspension of nitro compound (139 mg) and 10% Pd/C (75 mg) in abs EtOH (40 mL) was stirred at ambient temperature under 1 atm H$_2$ for 20 hr. The mixture was filtered (Celite) and the pad washed profusely with MeOH/CHCl$_3$ and HCl. Evaporation of the solvents afforded the crude amine as an orange-brown solid (125 mg, 97%). Recrystallization from MeOH/CHCl$_3$ gave the title compound as a tan-orange powder (87 mg, 67%), mp darkening above 250° C. with no discreet melting below 350° C. $^1$H NMR (DMSO-d$_6$) δ 0.88 (t, 3, J=7 Hz, H-18), 1.87 (m, 2, H-19), 5.22 (s, 2, H-5), 5.41, (s, 2, H-17), 5.74 (s, 2, NH$_2$), 6.18 (s, 2, —OCH$_2$O—), 6.47 (s, 1, OH), 6.91 (s, 1, H-14), 7.23 (s, 1, H-12), 8.74 (s, 1, H-7).

Example 2

CONVERSION OF 9-AMINO-10,11-MDCPT TO 9-GLYCINAMIDO-10,11-MDCPT HYDROCHLORIDE

A stirred mixture of the 9-amino compound (186 mg. 0.457 mmol) and BOC-glycine (150 mg, 0.85 mmol) in pyridine (1 mL) and DMF (15 mL) was chilled to 0° C. and treated with DCC (200 mg, 0.971 mmol). The mixture was warmed to ambient temperature and stirred for 65 hr. The solvents were evaporated and the residue dissolved in MeOH/CHCl$_3$, Celite (3 g) was added, the mixture evaporated, and the Celite-dispersed sample placed on a silica gel column (20 g). Elution (200 mL CHCl$_3$, 500 mL 5% MeOH/CHCl$_3$, 500 mL 12% MeOH/CHCl$_3$) and evaporation of appropriate fractions gave the intermediate BOC-protected derivative (98 mg, 38%). The derivative was treated with chilled conc HCl/dioxane (1:9, 5 mL), and the resulting mixture was stirred at ambient temperature for 5 hr. The solvent was evaporated, the residue sonicated in deionized H$_2$O (50 mL) and filtered (0.45 micron membrane). The clear yellow solution was lyophilized to give an amber gummy solid which on trituration with abs EtOH gave the glycinamide hydrochloride salt as a yellow microcrystalline solid (57 mg, 73%), mp darkening above 230° C. with no apparent melting below 340° C. IR $\nu_{max}$ (KBr) 3680–2300 with maxima at 3220, 2990 and 2920 (OH, amide H, amine HCl), 1740 (lactone), 1700 (amide), 1655 (pyridone), 1585, 1492, 1447, 1390, 1249, 1160, 1108, 1075, 1041, 933 and 845 cm$^{-1}$; $^1$H NMR (DMSO-d$_6$) δ 0.89 (t, 3, J=7 Hz, H-18), 1.87 (m, 2, H-19), 4.02 (d, 2, J=5.4 Hz, COC$\underline{H_2}$N—), 5.17 (s, 2, H-5), 5.42 (s, 2, H-17) 6.32 (s, 2, —OC$\underline{H_2}$O—), 7.26 (s, 1, H-14), 7.47 (s, 1, H-12), 8.38 (br s, 3, —NH$_3$), 8.59 (s, 1, H-7), 1075 (s, 1, amide H).

Example 3

SYNTHESIS OF 9-GLUTARAMIDO-10,11-MDCPT TRIETHANOLAMINE SALT

The 9-glutaramido derivative was synthesized from 9-amino-10,11-MDCPT by the following method:

9-Glutaramido-10,11-MDCPT.

A stirred suspension of 9-amino-10,11-MDCPT and glutaric anhydride in pyridine under nitrogen was heated at 95° C. for 2 hr. The solvent was removed from the brown solution by high vacuum distillation to give the crude amide as a brown gum. Purification was effected by chromatography through silica gel employing a solvent gradient from 5% methanol/chloroform to 50% methanol/chloroform. Evaporation of the appropriate fractions gave the 9-glutaramide half acid.

Alternatively, the 9-glutaramido derivative can be prepared by hydrolysis of its ethyl ester which is prepared by the following general method: 9-Amino-10,11-MDCPT in dry N,N-dimethylformamide containing pyridine is reacted at 0°–10° C. with a slight excess of ethylglutaryl chloride in N,N-dimethylformamide solution. After work-up and chromatography on silica gel, the 9-(ethyl)glutaramide derivative is obtained.

Example 4 synthesis of 9-(4-METHYLPIPERAZINO) CARBONYLAMINO-10,11-MDCPT HYDROCHLORIDE

The title compound was prepared from 9-amino-10,11-MDCPT in the following manner:

9-(4-Methylpiperazino)carbonylamino-10,11-MDCPT

9-Amino-10,11-MDCPT was added to chloroform (treated with alumina to remove hydroxylic components) containing triethylamine. The resulting solution was treated with phosgene gas and filtered to remove solids. The filtrate containing the intermediate carbamoyl chloride was treated with N-methylpiperazine under nitrogen and left overnight. The turbid mixture was washed several times with aqueous sodium bicarbonate solution, dried and evaporated to afford the crude title compound. Chromatography on silica gel provided 9-(4-methylpiperazino)carbonylamino-10,11-MDCPT.

9-(4-Methylpiperazino)carbonylamino-10,11-MDCPT Hydrochloride

The free base urea obtained above was suspended in methanol and treated with one equivalent of dilute aqueous hydrochloric acid. The methanol was evaporated and the aqueous residue filtered through a membrane filter. The sample was lyophilized to provide the title compound.

Example 5

SYNTHESIS OF 9-(N,N-DIETHYLAMINOETHOXY) CARBONYLAMINO-10,11-MDCPT

The intermediate 9-carbamoyl chloride was prepared as in the preceding example. The resulting chloroform solution was treated with N,N-diethylaminoethanol under nitrogen. After standing overnight, the mixture was washed with aqueous sodium bicarbonate solution, dried and evaporated to afford the crude carbamate. Purification by silica gel chromatography gave the pure title carbamate as the free base.

Example 6

9-(N,N-DIETHYLAMINOETHOXY)CARBONYLAMINO-10,11-MDCPT HYDROCHLORIDE

The free base from Example 5 was suspended in methanol and treated with one equivalent of dilute aqueous hydrochloric acid. The methanol was evaporated and the aqueous solution filtered (membrane). Lyophilization afforded the water soluble title carbamate.

Example 7

10,11-METHYLENEDIOXY-20(RS)-CAMPTOTHECIN SODIUM SALT (10,11-MDCPT SODIUM SALT)

The title compound was prepared from 10,11-methylenedioxy-20(RS)-camptothecin (Wani et.al., *J. Med. Chem.* 29, 2358 (1986)) by hydrolytic action of sodium hydroxide. Thus, 10,11-MDCPT (77 mg, 0.194 mmol) was suspended in 90% aqueous methanol (30 mL) and treated with 0.1 N aqueous sodium hydroxide (1.94 mL, 0.194 mmol). Upon heating at 50°–60° C. for 1 h under nitrogen a clear solution resulted which was cooled to ambient temperature and evaporated to dryness. The residue was dissolved in distilled water (2 mL) and filtered (0.45 micron membrane), and the resulting solution evaporated. The residue was recrystallized from ethanol/ether to provide the title compound as a pale yellow solid (53 mg, 65%), mp>300° C.; IR $\nu_{MAX}$ (KBr) 3400 (br), 2970, 2920, 1640, 1610, 1560–1580, 1497, 1466, 1370, 1246, 1225, 1183, 1030, 1000, 947, 855, 810, 761, 708 and 560–580; $^1$H NMR (DMSO-d$_6$) δ0.85 (t, 3, J=7 Hz, H-18), 2.09 (m, 2, H-19), 4.74 (ABq, 2, Δv=68 Hz, J=12, 4 Hz, H-17), 5.12 (s, 2, H-5), 5.64 (dd, 1, J =4, 7 Hz, 17-OH}, 6.17 (s, 1, 20-OH), 7.47 (s, 1, H-14), 7.54 (s, 1, H-9), 7.62 (s, 1, H-12), 8.41 (s, 1, H-7).

EXAMPLE 8

9-AMINO-10,11-METHYLENEDIOXY-20(RS)-CAMPTOTHECIN SODIUM SALT (9-AMINO-10,11-MDCPT SODIUM SALT

The title compound was prepared by an analogous alkaline hydrolysis of 9-amino-10,11-MDCPT which was prepared as described above. Thus, a suspension of 9-amino-10,11-MDCPT in aqueous methanol was warmed with one equivalent of aqueous sodium hydroxide to provide a clear solution. Isolation as above provided the water soluble title compound as an orange-yellow solid.

Obviously, numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the U.S. is:

1. A camptothecin analog having the structure shown below:

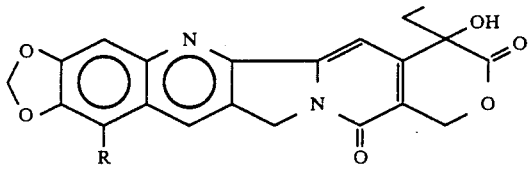

wherein R is $NO_2$, $NH_2$, $NHCOCHR^1 NR^2R^3$, where $R^1$ is the side-chain of an α-amino acid and $R^2$ and $R^3$, independently, are hydrogen or a lower alkyl group or $R^3$ is a peptide unit containing 1-3 amino acid units bonded to the nitrogen through a peptide bond, $NHCO\text{-}C_{2\text{-}8}\text{-alkylene-}X$ or $NHCO\text{-}C_{2\text{-}8}\text{-alkenylene-}X$, where X is COOH, $COO\text{-}C_{1\text{-}12}$ alkyl or $CONR\text{-}(CH_2)_n\text{-}NR^2R^3$, N=1-10 and $R^2$ and $R^3$ are as defined above, $NHCO\text{-}Z\text{-}(CH_2)_n\text{-}NR^2R^3$, where Z=oxygen or NH, or

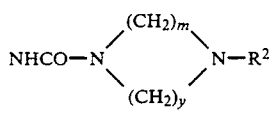

where M+y=3-6 and salts thereof.

2. The camptothecin analog of claim 1, wherein R is $NHCOCHR^1NR^2R^3$.

3. The camptothecin analog of claim 2, wherein $R^1$ is the side chain of a naturally occurring α-amino acid.

4. The camptothecin analog of claim 2, wherein $R^2$ and $R^3$ are, independently, hydrogen or a lower alkyl group having 1-6 carbon atoms.

5. The camptothecin analog of claim 2, wherein $R^3$ is a peptide unit containing 1-3 amino acid units.

6. The camptothecin analog of claim 2, wherein $R^1$ is a $C_{2\text{-}20}$ alkyl or aralkyl group.

7. The camptothecin analog of claim 1, wherein R is $NHCO\text{-}C_{2\text{-}8}\text{-alkylene-}X$ or $NHCO\text{-}C_{2\text{-}8}\text{-alkenylene-}X$.

8. The camptothecin analog of claim 7, wherein X is COOH.

9. The camptothecin analog of claim 7, wherein X is $CONR^2\text{-}(CH_2)_n\text{-}NR^2R^3$.

10. The camptothecin analog of claim 1, wherein R is $NHCO\text{-}Z\text{-}(CH_2)_n\text{-}NR^2R^3$ or

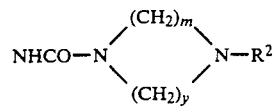

where Z is oxygen or NH and m+y=3-6.

11. The camptothecin analog of claim 10, wherein Z is oxygen and m+y=3-4.

12. The camptothecin analog of claim 10, wherein Z is NH and m+y=3-4.

13. The camptothecin analog of claim 1, wherein said salts are mineral acid or organic acid addition salts of a free amino acid group present in R.

14. The camptothecin analog of claim 1, wherein said salts are monovalent metal cation salts, ammonium salts or quaternary ammonium salts of a free acid group present in R.

15. The camptothecin analog of claim 1, wherein said salts have the structure shown below

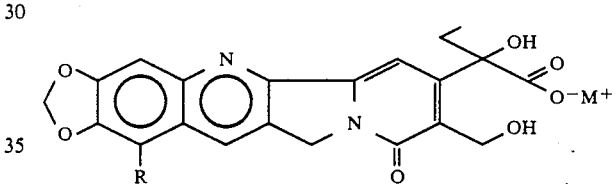

wherein M+ is a monovalent metal cation.

16. The camptothecin analog of claim 15, wherein M+ is a sodium cation.

17. The camptothecin analog of claim 1, wherein R is $NO_2$.

18. The camptothecin analog of claim 1, wherein R is $NH_2$.

* * * * *